Oct. 15, 1974 R. L. BYRUM Plant Pat. 3,639
ROSE PLANT
Filed Sept. 6, 1973
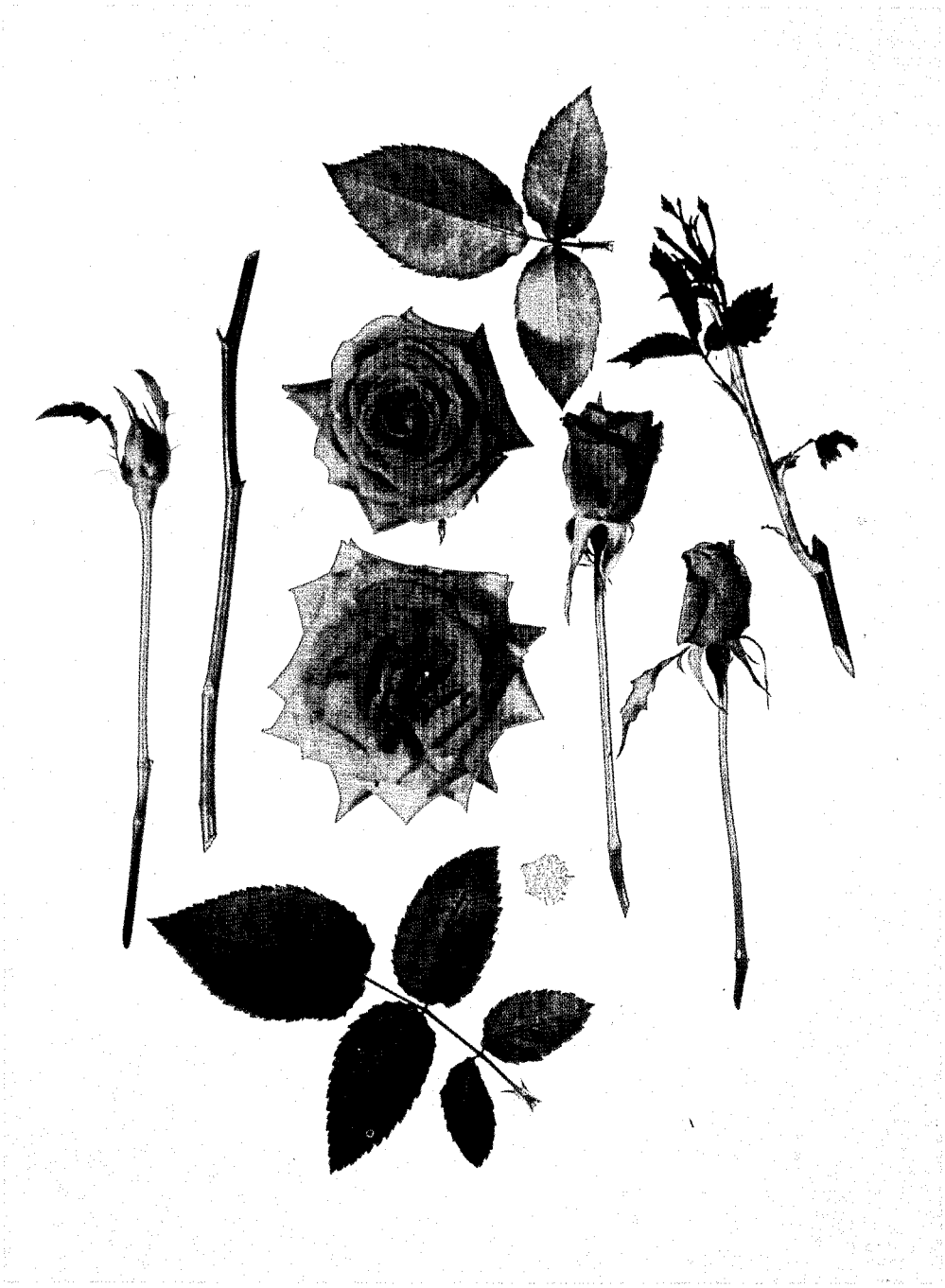

United States Patent Office

Plant Pat. 3,639
Patented Oct. 15, 1974

3,639
ROSE PLANT

Roy L. Byrum, Richmond, Ind., assignor to Joseph H. Hill Company, Richmond, Ind.

Filed Sept. 6, 1973, Ser. No. 394,629
Int. Cl. A01h *5/00*
U.S. Cl. Plt.—29 1 Claim

ABSTRACT OF THE DISCLOSURE

A new variety of floribunda hybrid rose plant for continuous greenhouse forcing distinguished by its abundant production of medium-small, well shaped, cardinal red to rose red blossoms on medium-strong 16 to 18 inch stems, its free growth habit and abundant foliage, the ability to break freely from a cut to produce from 55 to 60 blooms annually, and the ability to remain unaffected by dark cloudy weather so as to produce an unusually small amount of blind canes.

Background of the Invention

This new variety of rose plant originated as a seedling of Little Leaguer (P.P. 2,623) × Gemini (P.P. 2,728), the crossing having been made by me in the Spring of 1967 at Richmond, Ind., with the object of developing a more vigorous and more productive variety of a commercially standard rose type which would provide the Florist Industry with a year around quality product. The first flowering of plants of this new variety was in October 1968 and following extensive observation and test, this seedling was selected for propagation because it appeared to have the desired flower production and growth characteristics, as well as the good traits of both its parents. Asexual propagation of this new variety by budding has been carried on under my direction at Hamilton City, Calif., and at Richmond, Ind., and from generation to generation, the plants of this new variety have been observed to retain all of the distinctive characteristics of the original seedling wherefor these characteristics are deemed to be fixed and hold true from propagation to propagation.

Description of the Drawing

This new variety of rose plant is illustrated by the accompanying full color photographic drawing which shows the form of the opened flower and buds as well as face and reverse sides of typical leaves and young and old specimens of the wood, the color rendition being as nearly true as it is reasonably possible to accomplish through conventional commercial photographic procedures.

Description of the Plant

The following is a detailed description of this new variety of rose plant with color specifications according to Koster's Color Guide (K) and the Horticultural Colour Chart of Robert S. Wilson (W), published by The Royal Horticultural Society at London, England. All observations were made of plants and cut flowers grown in a greenhouse at Richmond, Ind.

THE PLANT

Origin: Seedling (#68–8R).
Parentage:
*Seed parent*—Little Leaguer (P.P. 2,623).
*Pollen parent*—Gemini (P.P. 2,728).
Classification:
*Botanical*—Rose Hybrid.
*Commercial*—Floribunda.
Form: Bush.
Habit: Upright and much branched.

Growth: Free, with canes of medium diameter.
Main Stems: Color—Sage Green, Plate 78 (K) overlaid with streaks of Maroon, Plate 97 (K). No thorns, prickles or hairs.
*Branches:* Color—Spinach Green 0960 (W). No thorns, prickles or hairs.
*New Shoots:* Nearest color—Deep Carmine Violet, Plate 46 (K). No thorns, prickles or hairs.
Foliage: Quantity—Abundant.
*Leaves:* Size—Medium large. Shape—Odd pinnate.
*Leaflets:* 3 to 5 in number. Shape: Elliptical with acuminate apex, round base, and simply serrate margin. Texture: Moderately heavy and leathery. Color: Mature, upper surface—nearest color Spinach Green 0960/1 (W). Mature, under surface—Lavender Green 000761 (W) overlaid with shades of Deep Carmine Violet, Plate 46 (K). Young, upper surface—Lettuce Green 861/2 (W) overlaid with shades of Deep Carmine Violet, Plate 46 (K). Young, under surface—nearest color Deep Carmine Violet, Plate 46 (K). Rachis: Medium light, with grooved upper side and prickly under side. Stipules: Short, narrow and with short points which turn out at an angle of more than 45°.

THE BUD

Before Calyx Breaks:
*Size:* Small.
*Form:* Short pointed ovoid with conspicuous neck with foliaceous appendages on the surface of the bud and much cut foliaceous parts extending beyond the tip of the bud at a distance of about three-quarters of the length of the bud.
*Color of Calyx:* Scheeles Green 860/1 (W).
As Calyx Breaks: Color of bud, outside of petal—Garnet Lake 828 (W).
As First Petal Opens:
*Size of Bud:* Small.
*Form:* Short pointed ovoid.
*Color of Petal:* Outside—Chrysanthemum Crimson 824/1 (W) washed or tinted with shades of Ruby Red 827/1 (W). Inside—Chrysanthemum Red 822 (W) overlaid with shades of Ruby Red 827/1 (W).
Bud Opening: Bud opens well.
Sepals: Permanent, spear shaped and of medium length.
*Color:* Inside—Scheeles Green 860/1 (W) with streaks of Pod Green 061 (W) through center. Outside—Scheeles Green 860 (W).
Peduncle: Strong, erect and of medium length and diameter.
*Bark:* Entirely smooth.
*Color:* Scheeles Green 860/1 (W). No thorns, prickles or hairs.

THE FLOWER

Blooming Habit: Continuous and abundant.
Size: Medium small, 2 to 2½ inches in diameter.
Borne: Singly, on long, medium-strong stems.
Shape: Full and high centered, with petals tightly rolled outward, when first opening, changing to open form with petals loosely rolled outward at maturity.
Petalage: Double, with 25 to 30 regularly arranged petals.
*Shape of Petals:* Ovate with retuse apex.
*Texture:* Moderately thick, with satiny inside surface and shiny outside surface.
*Color:* (a) A newly opened greenhouse flower in January 1973 at Richmond, Ind.:

*Outside Petal*

Outer surface: Nearest, Chrysanthemum Crimson 824/3 (W) overlaid with shades of Indian Lake 826/2 (W). Inside surface: Nearest, Cardinal Red 822/3 (W) overlaid with a velvety sheen.

*Intermediate Petal*

Outer surface: Nearest, Rose Red 724/3 (W), very slightly overlaid with shades of Indian Lake 826/2 (W). Inside surface: Nearest, Rose Red 724 (W).

*Inner Petal*

Outer surface: Nearest, Rose Red 724/3 (W). Inside surface: Nearest, Rose Red 724 (W).

(b) A flower opened 3 days in greenhouse in January 1973:

*Outside Petal*

Outer surface: Rose Red 724/2 (W) lightly washed or tinted with shades of Chrysanthemum Crimson 824/2 (W). Inside surface: Rose Red 724/2 (W) overlaid with shades of Chrysanthemum Crimson 824/2 (W).

*Intermediate Petal*

Outer surface: Tyrian Purple 727/1 (W). Inside surface: Rose Red 724 (W).

*Inner Petal*

Outer surface: Tyrian Purple 727/1 (W). Inside surface: Rose Red 724 (W).

(c) General color effect of open bloom: Newly opened flower: Cardinal Red 822/3 (W). Three day flower: Rose Red 724/2 (W).

Persistence: Petals hang on.

Fragrance: Slight tea.

Lasting Quality: Cut flowers—4 to 5 days kept at living room temperature.

REPRODUCTIVE ORGANS

Stamens: Medium number, regularly arranged about the pistils.

*Anthers:* Small, all open at the same time. Color: Amber Yellow 505/1 (W).

*Filaments:* Short, most filaments have anthers. Color: Empire Rose 0621/2 (W).

*Pollen:* Abundant. Color: Empire Yellow 603/3 (W).

Pistils: Medium number.

*Styles:* Short, uneven, bunched and moderately thin. Color: Carmine Rose, some 621 (W) and some 621/1 (W).

*Stigmas:* Color: Creamy White, Plate 2 (K).

Ovularies: Some protruding from calyx.

Hips: None.

Seeds: None.

This new variety of rose plant is particularly distinguished by its exceptionally good keeping qualities and vase life. There are very few, if any, disbuds; the plant has excellent vegetative growth from base to top of plant; and it breaks freely from a cut, producing up to 60 blooms, or more, annually. This plant is uneffected by dark cloudy weather and, therefore, produces an unusually small amount of blind canes.

This plant is similar to Mary De Vor, P.P. 2,838, but has a more profuse growth habit and a more rapid comeback from a cut with a better production of blooms. This plant is better than its seed parent in that it has longer stems, better retention of foliage, more abundant foliage, and larger flowers. This plant also improves on its pollen parent by producing longer stems and is commercially of more economic value because it is not a novelty variety.

I claim:

1. A new and distinctive variety of rose plant substantially as herein shown and described, characterized by its rapid vegetative growth and the ability to break freely from a cut to maintain a high production rate of about 60 flowers annually; by its small amount of blind canes due to dark cloudy weather; and by the longer stem length and good keeping qualities of its blooms.

No references cited.

ROBERT E. BAGWILL, Primary Examiner